United States Patent
Nissilä et al.

(10) Patent No.: US 6,432,061 B1
(45) Date of Patent: Aug. 13, 2002

(54) METHOD AND ARRANGEMENT FOR MEASURING VENOUS PRESSURE

(75) Inventors: Seppo Nissilä; Eija Vieri-Gashi, both of Oulu; Mika Sorvisto, Ylivieska; Mika Niemimäki, Oulu, all of (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 09/508,352
(22) PCT Filed: Sep. 14, 1998
(86) PCT No.: PCT/FI98/00719
§ 371 (c)(1),
(2), (4) Date: Mar. 9, 2000
(87) PCT Pub. No.: WO99/13768
PCT Pub. Date: Mar. 25, 1999

(30) Foreign Application Priority Data

Sep. 12, 1997 (FI) .................................................. 973679

(51) Int. Cl.⁷ ................................................. A61B 5/02
(52) U.S. Cl. ...................................... 600/500; 600/485
(58) Field of Search ................................ 600/485, 490, 600/491, 492, 493, 494, 495, 500, 502, 503, 504

(56) References Cited

U.S. PATENT DOCUMENTS

| 4,117,835 | A |   | 10/1978 | Williams ..................... 600/490 |
| 4,204,545 | A | * | 5/1980  | Yamakoshi .................. 600/506 |
| 4,566,462 | A | * | 1/1986  | Janssen ....................... 600/490 |
| 4,930,517 | A | * | 6/1990  | Cohen et al. ................ 600/484 |
| 4,938,227 | A |   | 7/1990  | Niwa et al. .................. 600/495 |
| 5,279,303 | A |   | 1/1994  | Kawamura et al. .......... 600/496 |
| 5,352,195 | A | * | 10/1994 | McEwen ....................... 604/66 |
| 5,447,161 | A |   | 9/1995  | Blazek et al. ................ 600/490 |
| 5,556,415 | A | * | 9/1996  | McEwen et al. .............. 606/202 |
| 5,690,119 | A |   | 11/1997 | Rytky et al. ................. 600/519 |
| 5,855,589 | A | * | 1/1999  | McEwen et al. .............. 606/202 |

FOREIGN PATENT DOCUMENTS

| DE | 26 05 528 A1 | 8/1977 |
| EP | 0 651 969 A3 | 5/1995 |
| EP | WO 97/03606  | 2/1997 |

\* cited by examiner

*Primary Examiner*—Kevin Shaver
*Assistant Examiner*—Charles Marmor, II
(74) *Attorney, Agent, or Firm*—Hoffmann & Baron, LLP

(57) ABSTRACT

The invention relates to a method and arrangement for measuring venous pressure. The measurement is made non-invasively by applying a variable compressive acting pressure to a measuring point, such as a person's extremity, at a compression point by a pressure generator, and at the same time the effect of the variable pressure on the circulation is measured at a second point located farther away from the heart, i e. closer to the end point of peripheral circulation than the compression point to which pressure is applied. The measured value of the acting pressure is transferred to an interpreting unit to which is also applied a pressure pulse caused by the heart and measured at said second point by a sensor to measure the effect of the variable acting pressure. In the interpreting unit venous pressure is determined on the basis of an acting pressure which is measured by a measuring element and which is the acting pressure when the interpreting unit detects a change in the pressure pulse signal measured by said sensor, the change being characteristic of venous pressure.

40 Claims, 4 Drawing Sheets

METHOD AND ARRANGEMENT FOR MEASURING VENOUS PRESSURE

BACKGROUND OF THE INVENTION

1. Field of the Invention

The invention relates to a method of measuring venous pressure.

The invention also relates to an arrangement for measuring venous pressure.

The heart pumps and causes blood to flow in the blood vessels, arteries and veins. The pumping produces pressure in the blood, i.e. blood pressure. Blood pressure is particularly affected by heartbeat and the resistance provided by peripheral circulation. Psychic factors, medication, smoking and other factors, such as a person's state, i.e. whether a person is asleep or awake, are also important.

2. Brief Description of the Related Art

The terms systolic pressure, diastolic pressure and venous pressure, are used when discussing blood pressure. Technically, from the point of view of measurement, systolic pressure refers to the pressure at which an artery becomes blocked, i.e. heartbeat stops. Physiologically, systolic pressure refers to the maximum pressure generated by a pumping cycle of the heart.

Technically, from the point of view of measurement, diastolic pressure refers to the pressure at which heartbeat is resumed when the pressure pressing the artery is reduced. Physiologically, diastolic pressure refers to the minimum arterial pressure value between two pumping cycles of the heart.

Venous pressure refers to the average pressure in a vein. At a certain stage of venous pressure measurement, a systolic and diastolic point can also be detected. Technically, from the point of view of measurement, venous pressure refers to such acting compressive pressure which, when acting, causes a vein to be occluded by the acting pressure. Occluded veins cause an increase in the tonus of the arm, i.e. an increase in the swelling of the arm, since once the arteries are occluded, blood remains in the arm as it has no way of returning. A typical value of venous pressure, measured from the arm, is between 20 and 30 mm Hg. The magnitude of venous pressure is indicative of the loading status of the heart, fluid balance and the condition of the circulation and blood vessels of the person who is the subject of the measurement.

Up to now, venous pressure has been measured invasively, i.e. intravenously from an artery. The drawback in the invasive method is naturally that the measurement is made from inside a person's body by the use of e.g. a catheter placed in a vein. The invasive method and the equipment solutions involved are unpleasant for a person, and the measurements involve much work and are cumbersome, since they require operating theater conditions. A special drawback is the risk of infection and bleeding of the artery. It has been known to use non-invasive methods, such as the auscultatory method, oscillometric method and manual palpation method for measuring diastolic and systolic pressure. The difficulty of the present venous pressure measurement method restricts the usability of measuring venous pressure in diagnostics. Venous pressure is measured mainly when the load of the atrium is observed during the filling state.

SUMMARY OF THE INVENTION

It is an object of the present invention to provide a new kind of method and arrangement for measuring venous pressure, avoiding the problems of known solutions.

This object is achieved by a method of the invention, characterized in that the measurement is made non-invasively by applying a variable compressive acting pressure to a measuring point, such as a person's extremity or the like, at a compression point by a pressure generator, and at the same time the effect of the variable acting pressure on the circulation is measured at a second point, the second point being located farther away from the heart, i.e. closer to the end point of peripheral circulation, than the compression point to which the acting pressure is applied, and that the measured value of the variable pressure acting on the measuring point at the compression point is transferred to an interpreting unit to which is also applied a pressure pulse caused by the heart and measured at said second point by a sensor to measure the effect of the variable acting pressure, and that in the interpreting unit venous pressure is determined on the basis of an acting pressure which is measured by a measuring element and which is the acting pressure when the interpreting unit detects a change characteristic of venous pressure in the pressure pulse signal measured by said sensor.

The measurement arrangement of the invention is characterized by comprising a pressure generator for applying a compressive acting pressure to a measuring point, such as a person's extremity or the like, at a compression point, the arrangement comprising a measuring element for non-invasive measurement of the acting pressure, and the arrangement further comprising an interpreting means for determining venous pressure, and the arrangement comprising a sensor for simultaneously non-invasively measuring the effect of the variable acting pressure on the circulation at a second point, said second point being located farther away from the heart, i.e. closer to the end point of peripheral circulation, than the compression point to which the acting pressure is applied, and said sensor which measures the effect of the variable acting pressure being a sensor which measures the pressure pulse generated by heartbeat and which is coupled to said interpreting unit to which is also coupled a measured signal indicating the measured value of the acting pressure, and the interpreting unit being arranged to determine the venous pressure non-invasively on the basis of an acting pressure which is the pressure acting when the interpreting unit detects a change characteristic of venous pressure in a pressure pulse signal measured by the sensor which measures the artery.

The method and measurement arrangement of the invention are based on the idea of using a sensor which measures arterial pressure pulse and transfers its measurement data to the interpreting unit to indicate from the measured acting pressure signal the point corresponding to venous pressure.

The solution of the invention provides a plurality of advantages. The invention provides an extremely good measurement accuracy, allowing the value of venous pressure to be determined extremely accurately, since its detection is based on a separate measurement of the pressure pulse, which is used to indicate the value of venous pressure. The result of the pressure pulse measurement depends on the change in the tonus of the measuring point, i.e. swelling, since as the tonus rises, the skin contact of the pressure pulse measuring sensor improves, whereby a rise in the measured amplitude of the pressure pulse is observed.

BRIEF DESCRIPTION OF THE DRAWINGS

In the following the invention will be described in greater detail with reference to the attached drawings, in which.

DETAILED DESCRIPTION OF THE INVENTION

Figure 1:
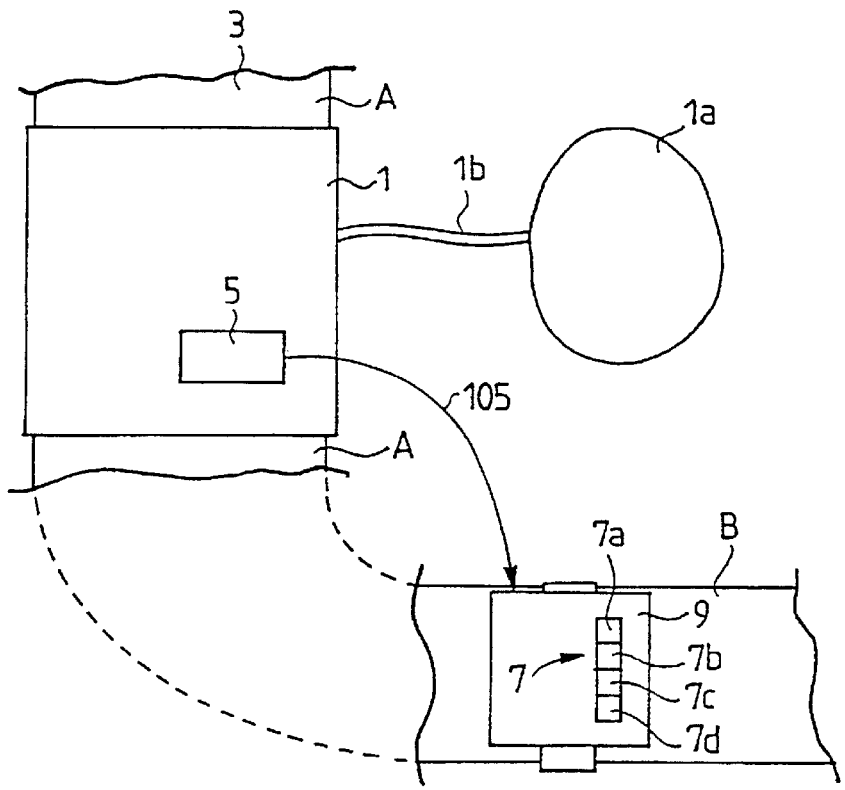
FIG. 1 shows a first embodiment of the measurement arrangement.

Referring to FIGS. 1 to 5, the invention relates to a method and an arrangement for blood pressure measurement. The measurement arrangement will be described first. The measurement arrangement comprises a cuff-like or other type of pressure generator 1, for applying pressure to a measuring point 3, such as a person's extremity 3 or the like, at a compression point A. The cuff-type pressure generator 1 obtains its pressure from a pressure source 1a, comprised by the arrangement, via a pressure line 1b. The pressure source 1a can be e.g. a pump.

The pressure serves to occlude the blood vessel by causing pressure to the extremity 3. The arrangement further comprises an element 5 for measuring the magnitude of the pressure generated by the pressure generator 1 for applying the pressure to the compression point A. The measuring element 5 can be e.g. a Si pressure sensor or other DC pressure sensor. The element 5 measuring the acting pressure is in connection with the pressure generator 1, i.e. the cuff 1.

The arrangement further comprises a sensor 7 for simultaneously measuring the effect of the variable acting pressure on an artery at a second point B. The sensor 7 can be e.g. a PVDF sensor (PolyVinylDiFluoride) or an EMF sensor (Electro Mechanical Film). Said second point B is a point which is farther away from the heart, i.e. closer to the end point of peripheral circulation than the compression point A, to which the pressure is applied. The measuring point B is thus at the distal, i.e. peripheral, side of the circulation. The measurement arrangement further comprises an interpreting means 9 for determining systolic and/or diastolic pressure. In other words, the measuring point B for the pressure pulse, i.e. heartbeat, sensor 7, is on the distal, i.e. peripheral, side of the circulation.

Said sensor 7 measures at the second point B the pressure pulse caused by heartbeat and is preferably separate from the pressure generator. The sensor 7 is coupled to said interpreting unit 9, to which a measuring signal, which is obtained from the measuring element 5 and depicts the measurement value of the acting pressure, is also coupled. Except for FIG. 9, the pressure pulse is preferably measured by a sensor 7 which, at least from the point of view of the technical operation of the measurement, is separate from the pressure generator, i.e. the sensor 7 measures the pressure pulse, i.e. the effect of the acting pressure, independently, not from the same signal source as the measuring element 5 measuring the acting pressure.

In some embodiments the sensor 7 can be in connection with the pressure generator or parts in connection therewith by e.g. a rod or conductor or otherwise, but in this case the pressure generator must be of a type which does not interfere with the operation of the sensor.

Figure 3:
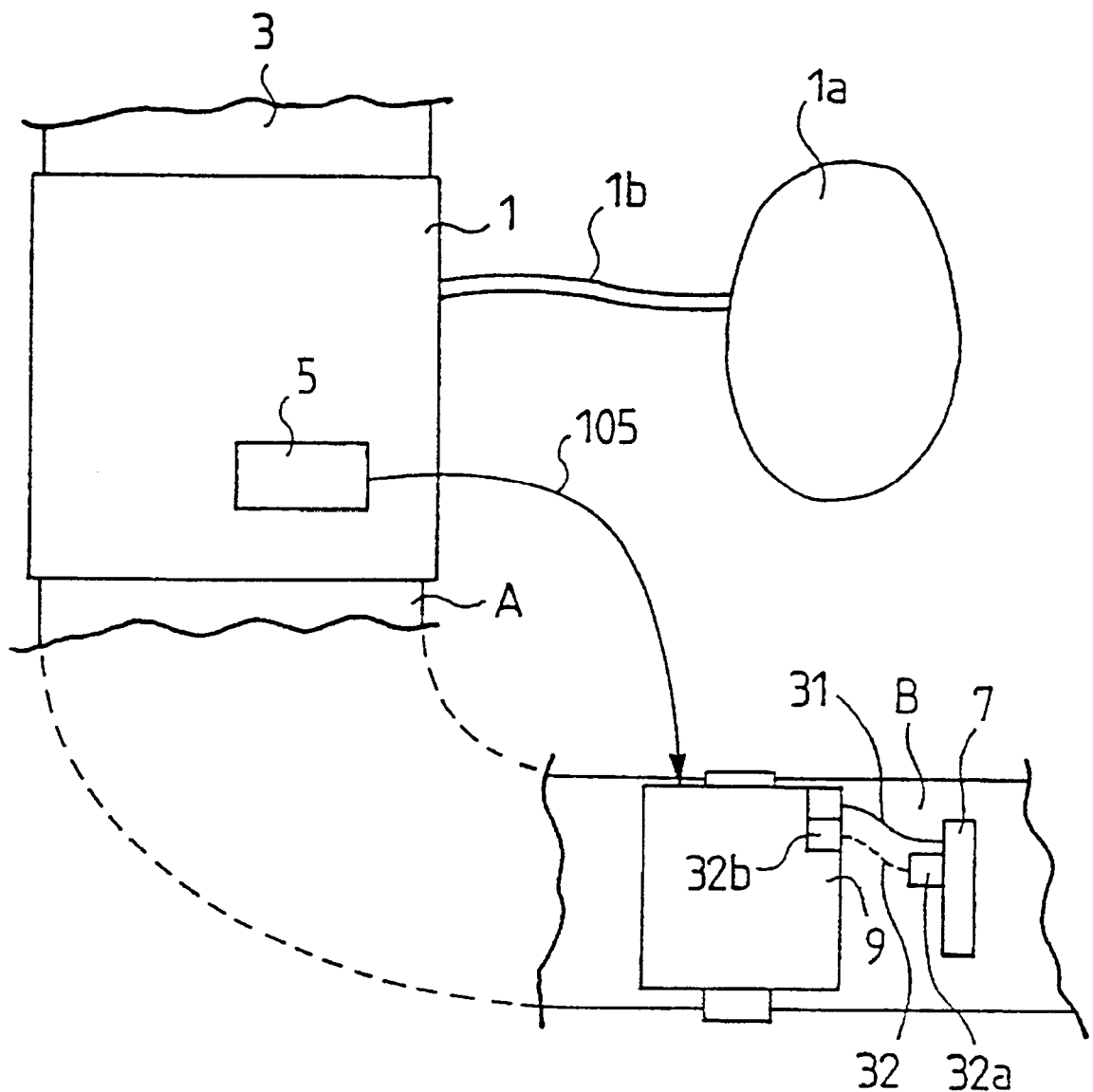
FIG. 3 shows a third embodiment of the measurement arrangement.

According to FIGS. 1 and 3, in the measurement arrangement the interpreting unit 9 is also preferably part of the wristband-type unit, or the interpreting unit forms a wristband-type unit 9, which in FIG. 1 comprises a pressure pulse sensor 7 for measuring the pressure pulse from point B. This makes the measurement arrangement well integrated and compact. In this preferred embodiment the method is such that the measured signal comprising the measured value of the acting pressure is transferred from the sensor 7 to said wristband type of interpreting unit 9, said interpreting unit 9 also being arranged to measure the pressure pulse by means of said pressure pulse measuring sensor 7 comprised by (FIG. 1) the interpreting unit 9 or being otherwise in connection (FIG. 3) therewith.

Figure 2:
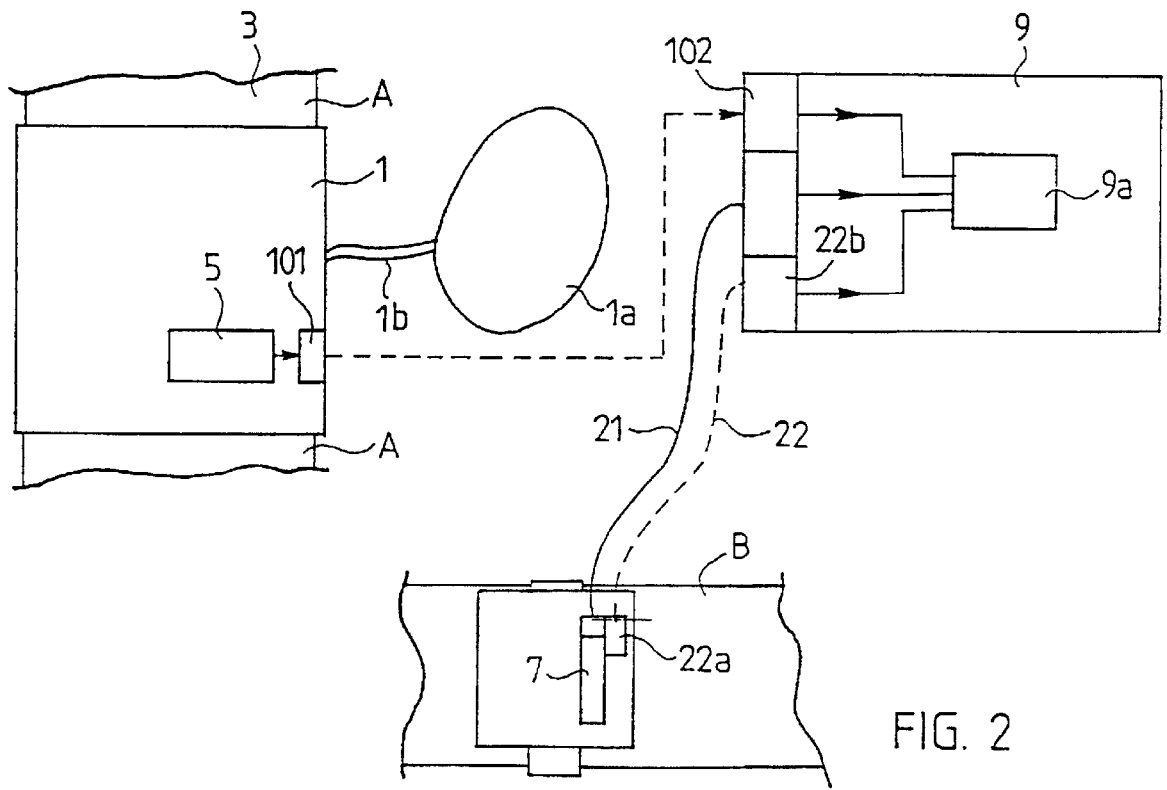
FIG. 2 shows a second embodiment of the measurement arrangement.

Referring to FIG. 2, an alternative solution can involve a separate interpreting unit, implemented by e.g. a microcomputer/measuring device or the like, the sensor 7 measuring the venous pressure pulse signal being in a wired connection 21 or in a wireless connection 22 with said interpreting unit 9. The wired connection 21 could be e.g. a cable 21 between the sensor 7 and the interpreting unit 9, i.e. a computer/measuring device provided with e.g. a measuring card. In FIG. 2, a dashed line 22 denotes a wireless connection between the arterial pressure pulse sensor 7 and the interpreting unit 9. The wireless connection 22 is preferably implemented by a magnetic inductive coupling 22a, 22b, comprising a transmitter element 22a controlled by the sensor 7 and comprising a coil, and a receiver element 22b disposed in the interpreting unit 9 and comprising a second coil. A suitable measuring card is e.g. National instruments DAQ-Card-700 to be placed in a PCMCIA card slot of a microcomputer.

A combination of the previous versions, i.e. a third embodiment in accordance with FIG. 3, is also feasible, i.e. the interpreting unit 9 is a wristband-type unit, but in FIG. 3 the pressure pulse sensor 7 for measuring the artery is not integrated with the interpreting unit 9, but is in a wired connection 31 or a wireless connection 32 with the interpreting unit 9. The connections 31, 32 can be implemented in the same way as was presented for the version of FIG. 2, i.e. by a cable 31 or as a magnetic inductive coupling 32. Reference numerals 32a, 32b denote the transmitter element 32a and receiver element 32b of the wireless telemetric magnetic inductive coupling.

In a preferred embodiment of the invention the pressure pulse sensor 7 is a multichannel sensor, most preferably a line sensor. The sensor 7 measuring the intravenous pressure pulse may comprise e.g. eight different sensor elements, of which four, for example, are in active use in the measurement. In this case the pressure pulse is measured as a multichannel measurement. This provides a more reliable measurement result than a single-channel sensor. In a preferred embodiment, the channel providing the best result is selected from these e.g. four actual measurement channels. The different channels 7a, 7b, 7c and 7d of an exemplary multichannel line sensor 7 are shown in FIG. 1 in a simplified form showing four measurement channels.

In a preferred embodiment, the pressure pulse is measured in the area of the radial artery, where the arterial pressure pulse is easily detectable, and which is a convenient point from the point of view of the subject of the measurement.

A measurement arrangement of the type described above provides a method for measuring venous pressure, in which method the measurement is made non-invasively by applying a variable, preferably rising, compressive acting pressure to a measuring point, such as a person's extremity or the like, at a compression point A by a pressure generator 1, and at the same time the effect of the variable acting pressure on the circulation is measured at a second point B. The rate of variation in the acting pressure can be e.g. 2 to 3 mm Hg/s. Said second point B is located farther away from the heart, i.e. closer to the end point of peripheral circulation than the compression point A to which pressure is applied. In the method, the measured value of the variable pressure acting on the measuring point at the pressing A point is transferred to an interpreting unit 9 to which the magnitude, preferably the amplitude, of the pressure pulse caused by the heart and measured at said second point B by a sensor 7 which is preferably separate from the pressure generator 1. Furthermore, venous pressure is determined in the method in the interpreting unit 9 on the basis of an acting pressure which is measured by the measuring element and which is the pressure acting when the interpreting unit 9 detects a change in the pressure pulse, in the magnitude, preferably the amplitude, of the pressure pulse signal measured by said sensor 7, said change being characteristic of venous pressure. The pressure pulse represents the heartbeat.

In the embodiments disclosed in the present application the pressure pulse is most preferably measured as an amplitude measurement, and naturally monitoring the magnitude of the pressure pulse is also based on monitoring amplitude values. However, instead of amplitude, the sensor 7 can measure the frequency or phase of the pressure pulse, which also serve to indicate the magnitude of the pressure pulse, and hence, amplitude. The measurement may also involve amplitude measurement, amplitude data being converted into frequency or phase data. Thus the present invention is not only restricted to direct amplitude measurement and comparison by means of amplitude.

As was stated above, the sensor 7 is preferably separate from the pressure generator 1, i.e. the cuff 1, whereby in the preferred embodiment the pressure pulse is measured with the sensor 7 from a point which is at least as far away from the pressure generator 1 as the point to which the reach area of the pressure oscillation of the pressure generator extends. In this case the pressure variation in the cuff 1 does not interfere with the measurement of the pressure pulse.

In the method, the measurement of the variable acting pressure with the measuring element 5 and the measurement of the pressure pulse, e.g. its amplitude, with the sensor 7, are used to form the magnitude of the pressure pulse, such as amplitude data, as a function of the acting pressure. Venous pressure is determined in the interpreting unit 9 on the basis of said function. The sensor 7, which is preferably physically completely separate from the pressure generator 1, i.e. the cuff 1, consequently operates as an indicator of the interpreting unit 9, indicating to the interpreting unit 9 the instant when the magnitude of the acting pressure of the cuff indicates the magnitude of the venous pressure.

Figure 4:
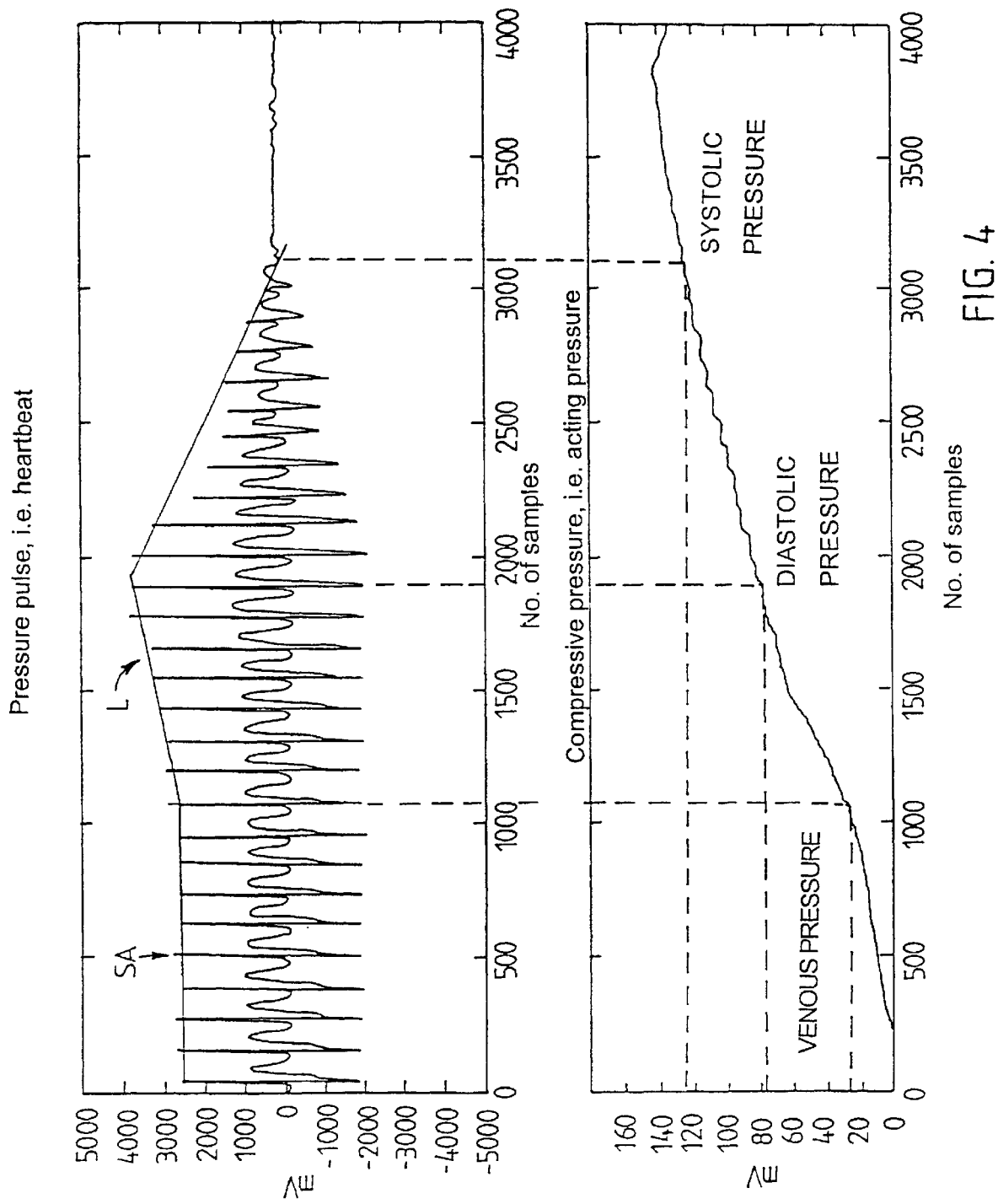
FIG. 4 shows measurement of venous pressure during rising pressure.

In a preferred embodiment in accordance with FIG. 4, said variable acting pressure is the rising acting pressure. In this case venous pressure is measured when the acting pressure is being raised by a pressure generator 1, that is, the cuff 1, for example. Measurement during rising pressure is more convenient to the subject, since the acting pressure does not have to be raised too high. A further advantage of using rising acting pressure is that the tonus in the arm increases linearly, the results of which can be easily detected by the sensor 7.

In this case venous pressure is most advantageously determined in a measurement during rising acting pressure on the basis of an acting pressure equal to the pressure acting when the interpreting unit 9 detects that the amplitude of the pressure pulse signal starts to increase when the sensor 7 measures the pressure pulse, e.g. its amplitude.

More specifically and still referring to FIG. 4, the method is preferably such that in a measurement made during rising acting pressure, venous pressure is determined on the basis of an acting pressure equal to the pressure acting when it is detected during measurement of the pressure pulse, e.g. its amplitude, that an essentially constant value of the pressure pulse starts to increase substantially linearly. In FIG. 4 said constant amplitude range is denoted by SA, and the linear range is denoted by L. It is easier to detect such points by the sensor 7 and the interpreting unit 9, and a more accurate measurement is also achieved. FIG. 4 also shows the points for diastolic and systolic pressure, which can be determined by the same methods and measurement arrangements as venous pressure.

Figure 5:
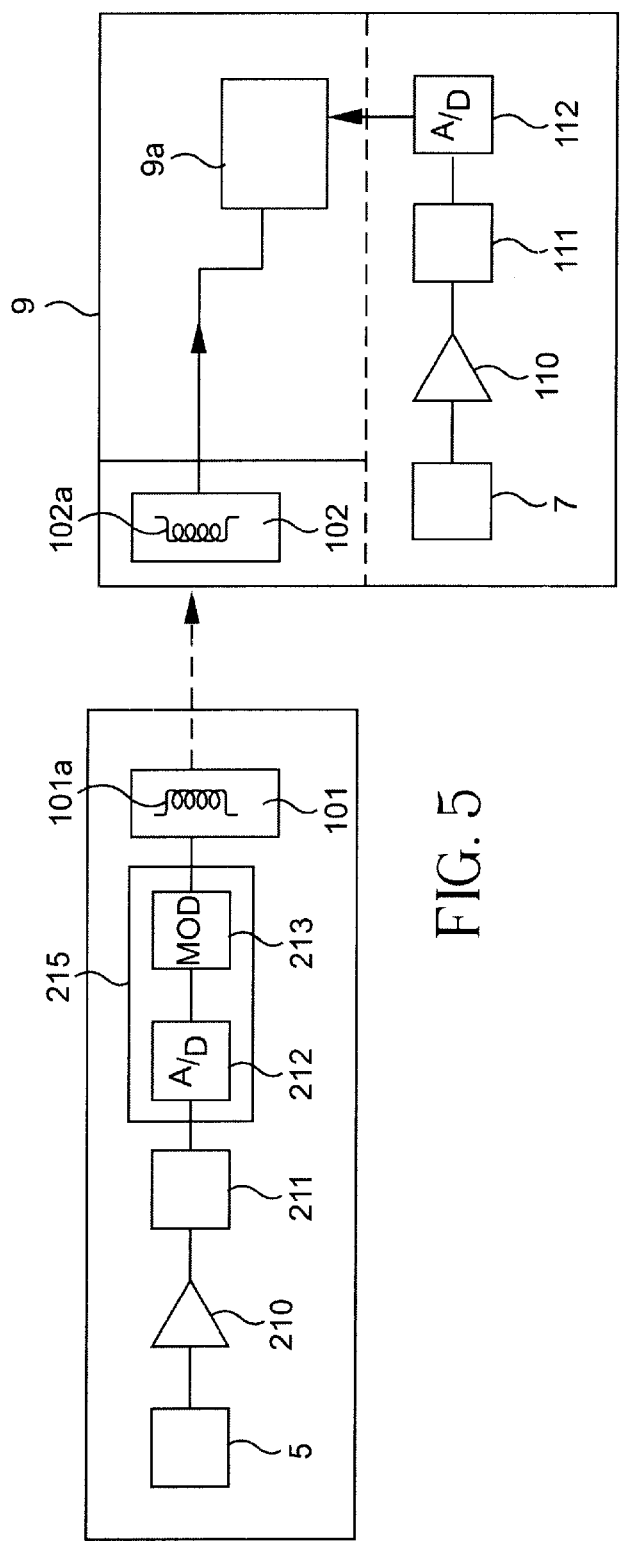
FIG. 5 shows an embodiment for transferring measurement data on the acting pressure and on the pressure pulse to the interpreting unit.

FIG. 5 shows an embodiment of the transfer of measurement data on the acting pressure to the interpreting unit 9, the acting pressure being measured by an acting pressure measuring element 5 in connection with the pressure generator 1, i.e. the cuff 1. FIG. 5 also shows another embodiment for processing a signal measured by the sensor 7 and for transferring said signal to the interpreting unit.

Referring to FIG. 5, a preferred embodiment of the invention involves a measurement arrangement comprising a wireless telemetric magnetic inductive coupling 101, 102 for transferring the measured acting pressure measuring signal from the measuring element 5 to the interpreting unit 9. Said coupling comprises a transmitter element 101, which obtains input data from the acting pressure measuring element 5, and a receiver element 102 in the interpreting unit 9. The transmitter element 101 comprises a coil 101a, to which the signal measured by the measuring element 5 is applied. The receiver element 102 comprises a second coil 102a. In the method the acting pressure measurement value is transferred to the interpreting unit 9 as a wireless telemetric transfer by means of the magnetic inductive coupling 101, 102 between the coils 101a, 102a. The connection 105 for transferring the signal measured by the acting pressure measuring element 5 to the interpreting unit 9, shown in FIGS. 1 and 3 in a simplified manner by arrow 105, can be a wired connection or wireless, as the transfer implemented by the inductive coupling by the components 101, 102 in FIGS. 2 and 5.

In accordance with FIG. 5, in a preferred embodiment the measurement arrangement comprises an amplifier 110 and a filter 111 for amplifying and filtering the pressure pulse signal measured by the sensor 7, and an A/D converter 112 for performing A/D conversion after filtering. The method is preferably such that the pressure pulse signal measured by the sensor 7 is amplified by the amplifier 110 and filtered by the filter 111, and then A/D converted by the converter 112. The amplification and filtering serve to eliminate interference and distortion, resulting in a sufficiently strong signal. The A/D conversion, in turn, converts the measured signal into a form which the interpreting unit 9 is able to interpret and process. FIGS. 2, 5 and 7 show the interpreting element 9a, e.g. a microprocessor, comprised by the interpreting unit 9. The versions shown by the other figures also comprise a similar component.

Figure 6:
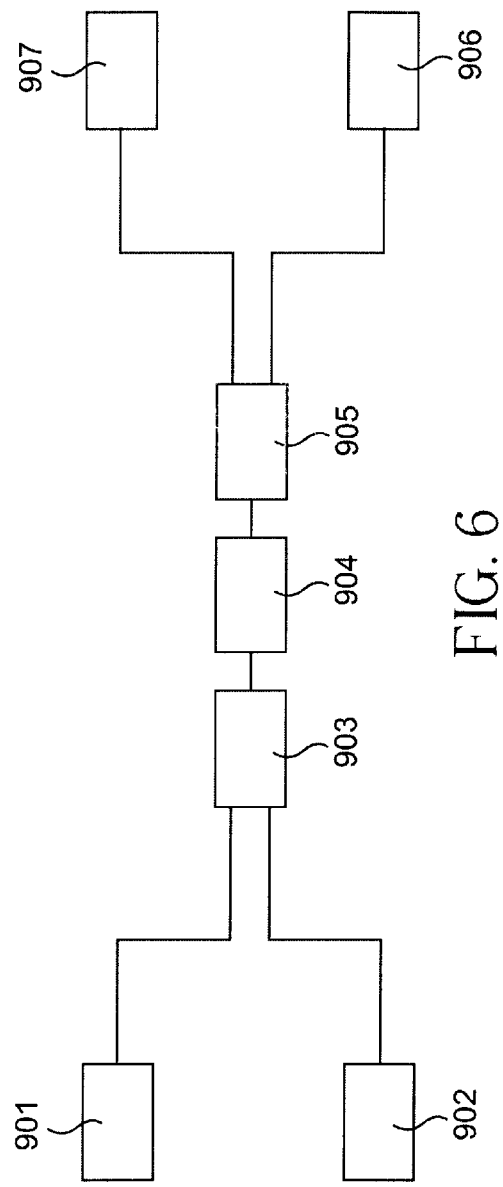
FIG. 6 shows the inner structure of the interpreting element comprised by the interpreting unit.

In fact, FIG. 6 shows the inner structure of the interpreting element 9a comprised by the interpreting unit 9. In FIG. 6, the interpreting element 9a comprises a part 901 for identifying the active pressure measurement signal, a part 902 for identifying the pressure pulse signal, a signal check part 903 connected to parts 901 and 902, a straight line fitting part 904 connected to part 903 and a SYS/DIAS determining part 905 connected to part 904. The SYS/DIAS determining part 905 determines the values of systolic and/or diastolic pressure according to what the straight line fitting algorithm (least squares principle) in the straight line fitting part 903 indicates on the basis of the received pressure measuring signal and pressure pulse signal. In a preferred embodiment the interpreting unit 9 comprises, or at least has a connection to, a memory 906 and a display 907. The memory 906 and the display 907 can be external parts with respect to the interpreting element 9a, belonging or being connectable, however, to the interpreting unit 9.

Referring to FIG. 5, in a preferred embodiment, the arrangement comprises a converter 210 and a filter 211 for filtering the measured acting pressure signal obtained from the measuring element 5 to filter off the oscillating AC portion and leave the measured filtered acting pressure signal. If an inductive coupling 101, 102, or some other transmitter unit/receiver unit 101, 102, is used for transferring the signal measured by the acting pressure measuring element 5 to the interpreting unit 9, then the arrangement further comprises a modulator 213 or another signal modulator unit 213 for modulating the A/D converted signal e.g. to a frequency modulated signal or to another signal which can be applied to the transmitter unit 101 comprised by the inductive coupling or e.g. an optical coupling 101, 102. Together the blocks 212 and 213 form a signal modulator 215 which serves to modulate the signal into a transferable form for the transmitter element 101. Said units 210 to 213 and 101 are most preferably part of the same entity as are the measuring unit 5 and the pressure generator 1. The method thus comprises a step of filtering the measured acting pressure signal by the filter 211 to filter off the oscillating AC portion caused by heartbeat, leaving the filtered measured acting pressure signal. In said preferred embodiment, the determination of venous pressure employs the filtered portion of the filtered acting pressure of the measured signal, obtained by filtration, and the information contained therein is transferred to the interpreting unit 9. The measured acting pressure signal is preferably amplified by the amplifier 210 before the measured acting pressure signal is filtered, and A/D conversion by the A/D converter 212 is carried out after filtration. In other words, the solution of the preferred embodiment employs in determining venous pressure an acting pressure signal which has been subjected to A/D conversion and from which the interpreting unit 9 calculates the blood pressure values from the measured signal originating from the measuring element 5 by using as indicator the signal of the sensor 7 measuring the artery. Thus the filtered measured acting pressure signal measured by the measuring element 5 in connection with the pressure generator 1, i.e. the cuff 1, is the acting pressure from which the arterial pressure pulse measuring sensor 7 "indicates" the value of venous pressure. Filtering off the AC portion of the measuring element 5 signal, i.e. the use of a filtered acting pressure, results in an acting pressure measurement result having less interference, since the effect of heartbeat, which causes AC oscillation in the acting pressure, on the cuff can be eliminated by filtration.

The magnetic inductive coupling described above in different contexts, is based on applying a current with varying magnitude to the coil of the transmitter element, the coil generating a magnetic field with varying magnitude, the field being received by a second coil, i.e. by the coil of the receiver element. A magnetic inductive coupling is useful in small portable devices owing to its low power consumption. An inductive coupling is particularly useful in wristband-type versions according to FIGS. 1 and 3.

The preferred embodiments of the invention described above and the other features of the method and measurement arrangement presented in greater detail highlight the advantages of the basic invention.

The above described different means can be implemented in manners considered optimal, e.g. by separate components, by processors implemented by software or other components implemented by software, or as a combination of said techniques, as a mixed technique, or in other manners available at each stage of technological progress.

Although the invention is described herein with reference to the examples in accordance with the accompanying drawings, it will be appreciated that the invention is not to be so limited, but can be modified in a variety of ways within the scope of the inventive idea disclosed in the appended claims.

What is claimed is:

1. A method of measuring venous pressure non-invasively, comprising:
    applying a variable compressive acting pressure to a measuring point, on an artery in a person's extremity, at a compression point by a pressure generator,
    measuring the effect of the viable acting pressure on the artery at a second point, the second point being located farther away from the heart, and closer to the end point of the artery than the compression point to which the acting pressure is applied,
    transferring a measured value of the variable pressure acting on the measuring point at the compression point to an interpreting unit,
    measuring a pressure pulse caused by the heart at said second point by a sensor to measure the effect of the variable acting pressure,
    transferring said pressure pulse measurement to said interpreting unit, and
    determining a venous pressure by said interpreting unit on the basis of an acting pressure which is measured by a measuring element wherein said acting pressure is equal to said venous pressure when the interpreting unit detects a change characteristic of venous pressure in the pressure pulse signal measured by said sensor.

2. A method as claimed in claim 1, characterized in that pressure pulse measurement data is generated as a function of the acting pressure on the basis of the measurement of the variable acting pressure employed in the method and the measurement of the pressure pulse, venous pressure being determined in the interpreting unit on the basis of said function.

3. A method as claimed in claim 1, characterized in that said variable acting pressure is a rising acting pressure, and that venous pressure is measured when the acting pressure is being raised.

4. A method as claimed in claim 3, characterized in that in the measurement performed during rising acting pressure, diastolic pressure is determined on the basis of an acting pressure equal to the pressure acting when it is detected in pressure pulse measurement that the magnitude of the pressure pulse starts to increase.

5. A method as claimed in claim 4, characterized in that in the measurement performed during rising acting pressure, venous pressure is determined on the basis of an acting pressure equal to the pressure acting when it is detected in pressure pulse measurement that the substantially constant value of the pressure pulse starts to increase substantially linearly.

6. A method as claimed in claim 1, characterized in that the pressure pulse is measured in the area of the radial artery.

7. A method as claimed in claim 1, characterized in that the pressure pulse is measured as a multichannel measurement.

8. A method as claimed in claim 7, characterized in that the pressure pulse is measured by a line sensor.

9. A method as claimed in claim 1, characterized by transferring the measured signal containing the measured value of the acting pressure to said wristband type of interpreting unit, which is also arranged to measure the pressure pulse by means of said pressure pulse measuring sensor comprised by it or otherwise being in connection thereto.

10. A method as claimed in claim 1, characterized by transferring the measured value of the acting pressure to the interpreting unit as a wireless telemetric transfer by means of a magnetic inductive coupling.

11. A method as claimed in claim 1, characterized in that the pressure pulse signal measured by the sensor is amplified and filtered, and then subjected to A/D conversion.

12. A method as claimed in claim 1, characterized in that the measured acting pressure signal is filtered to filter off an oscillating AC portion to generate a measured filtered acting pressure signal.

13. A method as claimed in claim 12, characterized in that the measured filtered acting pressure signal obtained by filtering the measured acting pressure signal is employed in determining venous pressure.

14. A method as claimed in claim 12, characterized in that before the measured acting pressure signal is filtered, it is amplified, and after filtration subjected to conversion to modify it to a transferable form.

15. A method as claimed in claim 14, characterized in that signal conversion preferably comprises A/D conversion, followed by modulation or corresponding modifying procedure.

16. A method as claimed in claim 1, characterized in that the pressure pulse is measured with the sensor from a point which is at least as far away from the pressure generator as the point to which the reach area of the pressure oscillation of the pressure generator extends.

17. A method as claimed in claim 1, characterized in that the pressure pulse is measured with a sensor which is separate from the pressure generator at least from the point of view of the technical operation of the measurement.

18. A method as claimed in claim 1, characterized in that the pressure pulse is measured with a sensor which is physically detached from the pressure generator.

19. A method as claimed in claim 1, characterized in that an inflatable cuff is used as the pressure generator.

20. A method as claimed in claim 1, characterized in that the sensor measures the amplitude, frequency or phase of the pressure pulse.

21. An arrangement for measuring venous pressure, comprising:
a pressure generator for applying a variable compressive acting pressure to a measuring point, on an artery in a person's extremity, at a compression point,
a measuring element for non-invasive measurement of the acting pressure,
an interpreting unit for determining venous pressure, and
a sensor for simultaneously non-invasively measuring the effect of the variable acting pressure on the artery at a second point, said second point being located farther away from the heart, and closer to the end point of the artery than the compression point to which the acting pressure is applied, and said sensor which measures the effect of the variable acting pressure being a sensor which measures the pressure pulse generated by heartbeat and which is coupled to said interpreting unit to which is also coupled a measurement signal indicating the measured value of the acting pressure, and the interpreting unit being arranged to determine the venous pressure non-invasively on the basis of an acting pressure which is the pressure acting when the interpreting unit detects a change characteristic of venous pressure in a pressure pulse signal measured by the sensor which measures the artery.

22. An arrangement as claimed in claim 21, characterized in that said interpreting unit is a wristband or other type of unit comprising said pressure pulse sensor.

23. An arrangement as claimed in claim 21, characterized in that said interpreting unit is a wristband or other type of unit which is in a wireless connection or a wired connection to said pressure pulse sensor.

24. An arrangement as claimed in claim 21, characterized in that the pressure pulse sensor is a multichannel sensor.

25. An arrangement as claimed in claim 24, characterized in that the pressure pulse sensor is a multichannel line sensor.

26. An arrangement as claimed in claim 21, characterized in that for transferring the measured acting pressure value to the interpreting unit, the arrangement comprises a wireless transmitter which receives input data from the acting pressure measuring element and wireless receiver element in the interpreting unit.

27. An arrangement as claimed in claim 26, characterized by comprising a signal modulator for modulating the filtered acting pressure signal into a form suitable for the transmitter element before the signal is coupled to the transmitter element.

28. An arrangement as claimed in claim 27, characterized in that the signal modulator comprises a signal modulator unit.

29. An arrangement as claimed in claim 28, characterized in that the signal modulator unit is a modulator selected from the group consisting of a pulse width modulator or a frequency modulator.

30. An arrangement as claimed in claim 28, characterized in that the signal modulator comprises an A/D converter which precedes the signal modulator unit and is used for A/D conversion of the measured filtered acting pressure signal.

31. An arrangement as claimed in claim 21, characterized in that for transferring the measured acting pressure value to the interpreting unit, the arrangement comprises a wireless telemetric magnetic inductive coupling comprising a wireless transmitter which receives input data from the acting pressure measuring element and a wireless receiver element in the interpreting unit.

32. An arrangement as claimed in claim 21, characterized by comprising an amplifier and a filter for amplifying and filtering the pressure pulse signal measured by the sensor, and an A/D converter for performing A/D conversion after the filtering.

33. An arrangement as claimed in claim 21, characterized by comprising a filter for filtering the measured acting pressure signal to filter off an oscillating AC portion for generating a measured filtered acting pressure signal.

34. An arrangement as claimed in claim 33, characterized in that before the filter, the arrangement comprises an amplifier for amplifying the measured acting pressure signal.

35. An arrangement as claimed in claim 33, characterized in that the filter which filters off the oscillating AC portion is a low-pass filter.

36. An arrangement as claimed in claim 35, characterized in that the upper limit frequency of the low-pass filter is between 1 and 5 Hz.

37. An arrangement as claimed in claim 21, characterized in that an inflatable cuff is used as the pressure generator.

38. An arrangement as claimed in claim 21, characterized in that the pressure pulse is measured by the sensor at a point which is at least as far away from the pressure generator as the point to which the reach area of the pressure oscillation of the pressure generator extends.

39. An arrangement as claimed in claim 21, characterized in that the pressure pulse is measured by the sensor which is separate from the pressure generator at least from the point of view of the technical operation of the measurement.

40. An arrangement as claimed in claim 21, characterized in that the pressure pulse is measured by a measuring sensor which is physically separate from the pressure generator.

* * * * *